Aug. 22, 1944. W. O. PROUTY Re. 22,534
ULTRAVIOLET LIGHT SOURCE
Original Filed March 23, 1931
Fig. 1
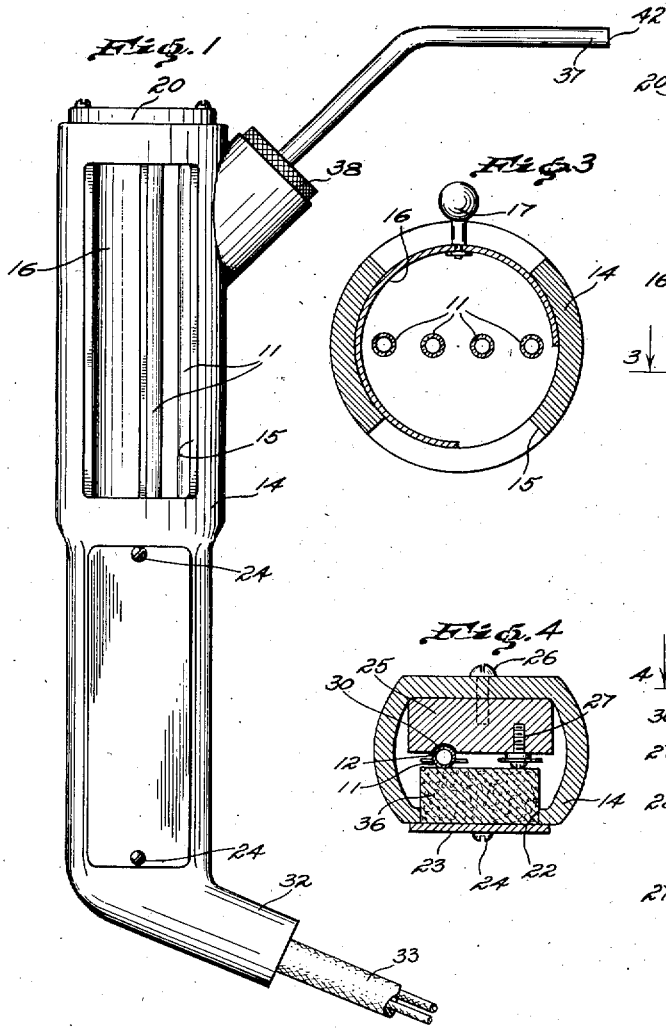
Fig. 3
Fig. 2
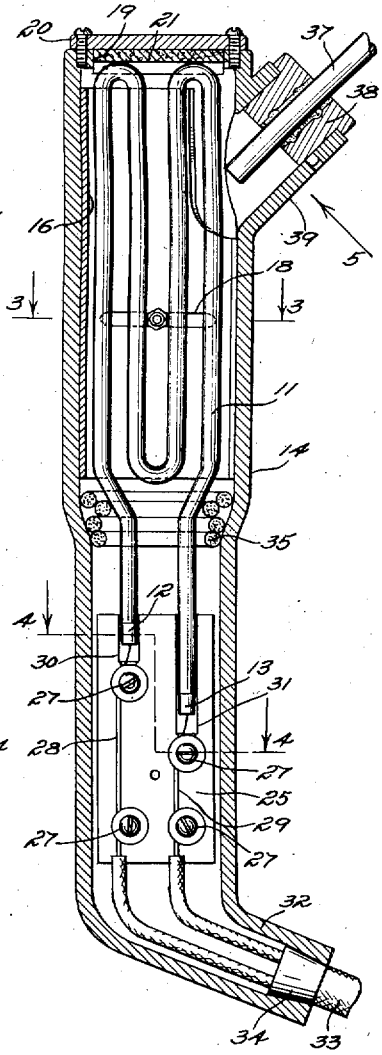
Fig. 4
Fig. 5
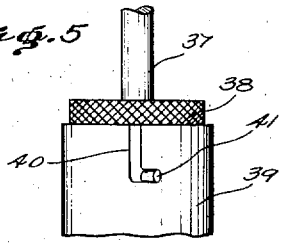
Inventor
Willis O. Prouty
by John Flam
Attorney Reissued Aug. 22, 1944

Re. 22,534

UNITED STATES PATENT OFFICE 22,534

ULTRAVIOLET LIGHT SOURCE

Willis O. Prouty, Hermosa Beach, Calif., assignor, by mesne assignments, to Westinghouse Electric and Manufacturing Company, New York, N. Y., a corporation of Pennsylvania Original No. 2,093,735, dated September 21, 1937, Serial No. 524,649, March 23, 1931. Application for reissue February 18, 1939, Serial No. 257,172

11 Claims. (Cl. 176—122)

This invention relates to a source of ultra-violet light, such as can be used for therapeutic purposes.

This application is a continuation in part of my prior application, Serial No. 448,128, filed April 28, 1930, and entitled "Therapeutic light."

In the said prior application, I point out the disadvantages encountered in ultra-violet light sources utilizing mercury arcs or carbon arcs. These disadvantages, in brief, can be summarized as follows: Such devices require excessive energy consumption; they become so hot that artificial cooling is required; and due to such high temperatures, it is difficult to keep the tube sealed when tubes are used. Furthermore, the apparatus is bulky and costly. In mercury tubes, due to the high temperatures of operation, there is a pronounced absorption effect of the ultra-violet emanations, making the device inefficient.

These disadvantages can be almost entirely avoided when a high-voltage discharge tube is used, having a filling of one or more of the noble monatomic gases. Such gases are now in common use, and include neon, argon, helium, and krypton. Discharge tubes having such a filling, stay cool and are compact.

Ordinarily neon or argon can be used as the gaseous filling, supplemented, although not necessarily, by the addition of a few drops of mercury to increase the ultra-violet radiations. I have found that the intensity of these emanations can be still further materially increased by proportioning the discharge tube in a manner that will be more specifically described hereinafter.

For example, in one series of comparative tests performed on a device incorporating my invention and a commercial mercury arc device, it was found that although the power consumed by my device was only about one-eighth that consumed by the mercury vapor device, yet my device emitted ultra-violet radiations in general much in excess of the mercury vapor device. The comparison was made at definite wave lengths of radiations; at wave lengths considerably above visibility, the intensities of the emanations from my device were very much greater than from the other device. Since the therapeutic effect of such short wave lengths is especially beneficial, it is seen that this feature is of considerable importance.

Accordingly it is one of the objects of my invention to make it possible to secure this intense radiation of ultra-violet light by the aid of a luminous discharge device.

My invention possesses many other advantages, and has other objects which may be made more easily apparent from a consideration of one embodiment of my invention. For this purpose I have shown a form in the drawing accompanying and forming part of the present specification. I shall now proceed to describe this form in detail, which illustrates the general principles of my invention; but it is to be understood that this detailed description is not to be taken in a limiting sense, since the scope of my invention is best defined by the appended claims.

Referring to the drawing:

Fig. 1 is a side elevation of an ultra-violet ray device embodying my invention;

Fig. 2 is a longitudinal, sectional view thereof;

Fig. 3 is a detail section taken along plane 3—3 of Fig. 2;

Fig. 4 is a detail section taken along plane 4—4 of Fig. 2; and

Fig. 5 is a detail view taken in general in the direction of the arrow 5 in Fig. 2.

The source of ultra-violet radiations is shown as a tube 11 which is doubled one or more times on itself. This tube is shown as provided at its extremities with the small internal electrodes 12 and 13, but other forms of electrodes could be used if desired. This tube can be filled with any of the noble monatomic gases or mixtures thereof to a pressure of a few millimeters of mercury, say from four to twelve millimeters. A few drops of liquid mercury can also be inclosed inside the tube. This tube is made from material that can readily pass the ultra-violet rays, such as quartz. The tube 11 can, furthermore, be kept comparatively small, its doubled length in most instances not exceeding 10 or 12 inches, although the length of the tube 11 can be varied to suit conditions.

In order to obtain the best and most intense effects from the tube 11, its inner diameter should not exceed seven millimeters; the preferable value is about three or four millimeters. It should be operated below a current consumption of 50 milliamperes, and a potential difference across it above 1000 volts. Apparently the small diameter obviates material self-absorption of the rays, and the low current consumption, while sufficient to cause the gas to luminesce, yet serves to leave the tube 11 cool enough to be readily handled by an operator without artificial cooling, inasmuch as its operating temperature is inherently below 50° C. which is but slightly above body temperature, and which, as is well recognized from International Critical Tables, gives a mercury pressure of not more than 13 microns during operation of the device.

In order to house the tube 11 and provide terminals for connection to the electrodes 12 and 13 I may utilize a casing 14. This casing may be made from a casting such as aluminum. Its top portion may be generally cylindrical and is preferably formed with an opening 15 through which the tube 11 can be exposed. In the present instance, the width of the opening can be varied, as by a shutter 16 which conforms with the interior surface of the casing, and which can be manipulated as by a handle 17 extending through a slot 18 in the back of the casing. If desired the interior surface of this shutter can be polished to act also as a reflector.

In order to permit the tube 11 to be inserted into the casing 14 there is provided a top opening 19. This opening can be closed by cover member 20. In order to steady the tube 11 this cover member may carry a cushion or pad, such as 21, made of sponge rubber or the like.

In the present instance, the lower portion of frame 14 can be flattened, as indicated most clearly in Fig. 4. In this lower portion there is a large opening 22 that can be covered up by cover plate 23. This cover plate can be fastened in place by screws 24.

Terminal block 25 can be accommodated in the lower portion of the casing and can be held in place as by the aid of one or more screws 26. This terminal block can be made of any appropriate insulation material. It carries a number of screws 27, engaging the conductors 28, 29 that lead to the electrodes 12 and 13. The extremities of the tube 11 can be accommodated in shallow pockets, such as 30, 31 in the front face of the block 25.

The conductors 28 and 29 can extend downwardly below block 25. They can pass through the neck 32 to the exterior, and are shown in Fig. 2 as carrying heavy insulation, forming the twin conductor 33. A plug 34 can be used to maintain this conductor 33 in place in the neck 32.

In order further to support the tube 11 against dislodgement I may utilize several turns of asbestos rope 35 encompassing both bends of the tube 11 near the lower portion thereof. Sponge rubber cushion 36 can be fastened to the cover 23 (Fig. 4) for holding these extremities in the pockets 30, 31.

For the application of the ultra-violet rays to a comparatively large surface, the opening 15 can be used. The size of the opening can be adjusted by manipulation of handle 17, the hand of the manipulator grasping the lower portion of the casing 14.

For more confined treatment I can provide a tubular extension 39, at an angle to the casing axis, through which the upper part of the tube 11 can be exposed. If desired, a supplemental applicator confining the area treated still further, can be supported in extension 39. One example of such applicators is indicated in Figs. 1, 2, and 5. It includes a quartz rod 37. This quartz rod is cemented in a metal collar 38, which is adapted to be disposed near the tube 11. In order to support the collar 38 detachably in this projection 39, this extension can be provided with a bayonet slot 40 for accommodating pin 41 extending radially of the collar 38.

In the present instance this applicator 37 is shown merely as a bent rod which is made of quartz, and which has the property of conducting the ultra-violet radiations from inside casing 14 to the extremity or tip 42 of the rod, without substantial dispersion transverse to the rod. The tip 42 of the applicator can therefore be directed against the locality to be treated.

I believe that the effectiveness of this tube results mainly from the small current consumption and small cross-sectional area. The small area ensures against interference and reabsorption or change of wave length, and the small current consumption, because it keeps the tube cool, also contributes to the same end.

I claim:

1. In a device for producing ultra-violet radiations having a high intensity in the wave band from 2000 to 2540 Angstrom units, a tube capable of passing such radiations, said tube having an internal diameter no greater than seven millimeters, a filling for the tube of one or more noble monatomic gases, and means for impressing an energizing potential difference across the column of gas in the tube.

2. In a device for producing ultra-violet radiations having a high intensity in the wave band from 2000 to 2540 Angstrom units, a tube capable of passing such radiations, said tube having an internal diameter no greater than seven millimeters, a filling for the tube of one or more noble monatomic gases, and means for impressing an energizing potential difference across the column of gas in the tube, to produce a current flow therein not exceeding fifty milliamperes.

3. In a device for producing ultra-violet radiations having a high intensity in the wave band from 2000 to 2540 Angstrom units, a tube capable of passing such radiations, said tube having an internal diameter no greater than seven millimeters, a filling for the tube of one or more noble monatomic gases, and means for impressing an energizing potential difference across the column of gas in the tube, said potential difference being no less than one thousand volts.

4. In a device for producing ultra-violet radiations having a high intensity in the wave band from 2000 to 2540 Angstrom units, a tube capable of passing such radiations, said tube having an internal diameter between three and four millimeters, a filling for the tube of one or more noble monatomic gases, and means for impressing an energizing potential difference across the column of gas in the tube, to produce a current flow therein not exceeding fifty milliamperes.

5. The process of producing ultra-violet radiations having a high intensity lying in the wave band from 2000 to 2540 Angstrom units, by the aid of a luminous column of noble monatomic gases, which comprises energizing said gas column, and confining the column to a diameter no greater than seven millimeters.

6. The process of producing ultra-violet radiations having a high intensity lying in the wave band from 2000 to 2540 Angstrom units, by the aid of a luminous column of noble monatomic gases, which comprises energizing said gas column, and reducing self-absorption in the column by restricting the diameter of the column.

7. The process of producing ultra-violet radiations having a high intensity lying in the wave band from 2000 to 2540 Angstrom units, by the aid of a luminous column of noble monatomic gases, which comprises energizing said gas column, confining the column to a diameter no greater than seven millimeters, and restricting the current flow through the column to a value not exceeding fifty milliamperes.

8. The process of producing ultra-violet radiations having a high intensity lying in the wave band from 2000 to 2540 Angstrom units, by the aid of a luminous column of noble monatomic gases, which comprises energizing said gas column, and confining the column to a diameter between three and four millimeters.

9. An ultra-violet lamp for producing ultra-violet radiations having a high intensity in the wave band of 2000 to 2540 Angstrom units comprising an envelope containing a gaseous filling at a pressure of at least 4 millimeters including mercury vapor and an inert gas, and means for impressing an energizing potential across said lamp to cause luminescence of said gaseous filling and to produce a current flow therein sufficient to maintain the operating temperature of said lamp at approximately 50° C. whereby the mercury vapor is maintained at a pressure not greater than 13 microns.

10. The method of operating an ultra-violet lamp for producing ultra-violet radiations having a high intensity in the wave band of 2000 to 2540 Angstrom units and provided with an envelope containing a gaseous filling including mercury vapor and an inert gas, which consists in impressing across the lamp an energizing potential sufficient to cause luminescence of the gaseous filling, and restricting the current consumption of said lamp to a value such that the operating temperature of the lamp is maintained at approximately 50° C. and thus cool enough to be readily handled, and the mercury vapor pressure during operation is maintained at approximately 13 microns.

11. A discharge lamp for producing ultra-violet radiations having a high intensity in the wave band of 2,000 to 2,540 Angstrom units comprising an envelope containing a gaseous filling including mercury vapor and an inert gas, and means for impressing an energizing potential across said lamp to cause luminescence of said gaseous filling and to produce a current flow therein sufficient to maintain the operating temperature of said lamp at approximately 50° C. and the mercury pressure at approximately 13 microns.

WILLIS O. PROUTY.